United States Patent [19]

Christian et al.

[11] Patent Number: 5,269,370
[45] Date of Patent: Dec. 14, 1993

[54] THERMAL CYCLING DEVICE

[75] Inventors: Earl L. Christian, San Diego, Calif.;
Kyle C. Owen, Arlington, Tex.

[73] Assignee: General Dynamics Corporation,
Space Systems Div., San Diego, Calif.

[21] Appl. No.: 676,687

[22] Filed: Mar. 28, 1991

[51] Int. Cl.[5] .................... G01N 3/60; G01N 25/72;
F25B 29/00
[52] U.S. Cl. .................................. 165/61; 432/53;
432/56; 432/77; 432/85; 374/57; 374/45;
62/78; 62/64
[58] Field of Search .................. 165/61; 62/64, 78;
432/53, 56, 77, 85; 374/57

[56] References Cited

U.S. PATENT DOCUMENTS

| | | | |
|---|---|---|---|
| 2,746,740 | 5/1956 | Weaver | 432/56 |
| 3,365,930 | 1/1968 | Arais | 374/57 |
| 3,447,788 | 6/1969 | Bornor | 432/56 |
| 3,503,595 | 3/1970 | Olson et al. | 432/53 |
| 3,588,060 | 6/1971 | Hermans | 432/53 |
| 3,598,381 | 10/1971 | Schwalm | 432/53 |
| 3,753,357 | 8/1973 | Schwartz | 62/64 |
| 3,972,704 | 8/1976 | Loxley et al. | 432/77 |
| 4,575,257 | 3/1986 | Ogura et al. | 165/61 |
| 4,779,163 | 10/1988 | Bickford et al. | 374/57 |
| 4,827,736 | 5/1989 | Miura et al. | 62/78 |
| 4,846,717 | 7/1989 | Jiménez-Maldonado | 432/85 |
| 5,000,682 | 3/1991 | Heidt et al. | 432/56 |
| 5,038,571 | 8/1991 | Yokouchi et al. | 62/64 |

FOREIGN PATENT DOCUMENTS

| | | | |
|---|---|---|---|
| 2360032 | 7/1974 | Fed. Rep. of Germany | 62/64 |
| 0295942 | 12/1988 | Japan | 374/57 |

*Primary Examiner*—John K. Ford
*Attorney, Agent, or Firm*—Frank D. Gilliam; John R. Duncan

[57] ABSTRACT

A thermal cycling apparatus having an upper heat chamber and a lower cold chamber positioned vertically beneath the upper heat chamber and vertically coaxial therewith whereby a material to the thermal cycle tested can be transferred between the upper heat chamber and the lower cold chamber. An externally operated flapper door within the thermal cycling apparatus separates the two chambers. The material to be thermally tested is placed in a basket constructed of suitable material which can be translated between the two chambers from a location externally of the chambers. The temperature in the upper chamber is elevated by gaseous nitrogen to a temperature up to about 1000 degrees F. and the lower cold chamber is cooled by a cryogenic liquid. Cycle testing is preformed by alternately transferring the material, i.e. 40 or more specimens at a time, between the upper and lower chambers the number of times desired.

8 Claims, 3 Drawing Sheets

THERMAL CYCLING DEVICE

BACKGROUND OF THE INVENTION

The invention is directed to thermal cycling of material(s) and more particularly to thermal cycling of material(s) between an extremely large range of temperatures.

Vehicles for flights into space and satellites launched therefrom require the use of materials that can endure a large range of temperature change between the temperature on earth prior to launch, the temperature of outer space and the re-entry heat generated upon exposure to the earths atmosphere on return to earth. The selection of construction materials of these vehicles and satellites is especially critical primarily to insure the safety of humans which travel into space and return within the space vehicle, the extremely high cost encountered in the construction of the space craft and its payload and satellites are secondary economic considerations.

Although materials have been previously thermal cycle tested by placing them in evacuated or inert gas filled ovens where the temperature is elevated to a desired level and then removing the material from the oven and quenching the material into a super cooled liquid this method can be very dangerous and time consuming when many cycles from hot to cold and cold to hot is required and does not provide good temperature cycling control. In addition to the operators great exposure to danger especially when the cooling liquid is liquid hydrogen, a considerable amount of time is required and a considerable waste of super cooled liquid occurs due to boil off both of which are economically very expensive. When the material to be tested is of the type requiring heating in an inert atmosphere the material must be reduced in temperature prior to exposure to the atmosphere and the super cooled liquid. This requires considerable time for cycling and results in a test which does not truly cycle the material instantaneously between extreme heat and extreme cold within the temperature range required for the test.

Additional consideration must be directed to the safety of the personal operating the thermal cycling testing to prevent injury to them in the handling of volatile materials such as, liquid hydrogen, and the possibility of explosion.

There has not been an operator safe and successful means for thermal testing of material(s) between an extreme hot and cold temperature range until the emergence of the instant invention.

SUMMARY OF THE INVENTION

The present invention is directed to a thermal cycling apparatus for the hot and cold testing of materials in the range of +1000 degrees F. to −453 degrees F. which can be safely operated by personal externally of the testing apparatus.

The apparatus comprises of a pair of coaxial vertically positioned chambers one on top of the other. A heating chamber is positioned at the top of the vertically stacked chambers and a cooling chamber is positioned at the bottom thereof. A door is positioned between the two chambers. The upper chamber is heated by a admitting heated gaseous nitrogen into the chamber at a predetermined desired temperature level and the lower chamber contains a cryogenic liquid, i.e. Nitrogen, Hydrogen, Helium or the like at a temperature down to −453 degrees F. The material(s) to be temperature cycled is positioned in a basket formed of a material suitable for the desired temperature range from + to − which is translatable between the two chambers by external means. The door between the chambers is also opened and closed by external means. The basket can be translated therebetween and the door opened and closed either manually or by automatic control means such as, a computer controlled motor or the like. The door serves as a barrier between the two chambers preventing a leak of the boil off gases of the liquid into the upper chamber when the heat is being applied to the material(s). A leak tight seal is provide between the door and its seat positioned on the top surface of the lower chamber. Hydraulic clamps are used to hold the door closed against its seat to insure a satisfactory seal of the lower chamber by the door and its seat. Purge ports are provided to remove all moisture containing gas from the upper chamber prior to the opening of the door between the chambers to prevent any moisture from entering the lower chamber where freezing of that moisture would occur. The upper chamber is also tested for explosive gases such as hydrogen when liquid hydrogen is used for cooling prior to removal of the specimen(s) from the upper chamber via sniffer ports to insure a complete absence of hydrogen within the upper chamber. The specimen(s) is removed by the removal of an upper lid from the chamber.

For cycle testing the specimen(s) of material is placed into the basket and positioned in the upper chamber where the specimen(s) is heated to a desired temperature. The maximum desirable temperature being in the range of +1000 degrees F. Once the specimen(s) reaches the desired elevated temperature, the source of heat is terminated and the basket is lowered into the liquid hydrogen through the now opened door. Upon achieving the temperature of the liquid hydrogen, the basket is raised out of the liquid hydrogen through the open door. The door is again closed and sealed and the source of heat is again supplied to the upper chamber and the hot cold cycle is repeated until the desired number of cycles are achieved and the test is completed.

After the test is completed the upper chamber is tested and any residual gas present therein is purged or removed, the chamber lid is removed and the basket and material(s) is then removed.

The temperature of the specimen(s) is controlled by conventional thermal couples or other suitable temperature monitoring devices.

An object of this invention is to provide a personnel safe means and method for thermal cycle testing of material specimen(s).

Another object of this invention is to provide a positive temperature controlled cycling of material specimen(s).

Still another object of this invention is to produce a thermal testing device that can subject specimen(s) of material between +1000 degrees F. and −453 degrees F.

These and other objects and advantages of the present invention will become apparent to those skilled in the art after considering the following detailed specification in which the preferred embodiment are described in conjunction with the accompanying drawing Figures.

BRIEF DESCRIPTION OF THE DRAWING FIGURES

DETAILED DESCRIPTION OF THE PREFERRED EMBODIMENT OF THE INVENTION

The following discussion is primarily directed to the cycling of material by using gaseous nitrogen as the heating source and liquid hydrogen as the super cooled liquid. It should be understood that any suitable heat source or super cooled liquid can be used to practice this invention and the particular heating source or cooling liquid is not intended to limit this invention in any way but are chosen for ease of explanation of the details of this invention.

It should be understood that hereinafter the terms specimen and material are used to denote one or more specimens of materials being tested.

Figure 1:
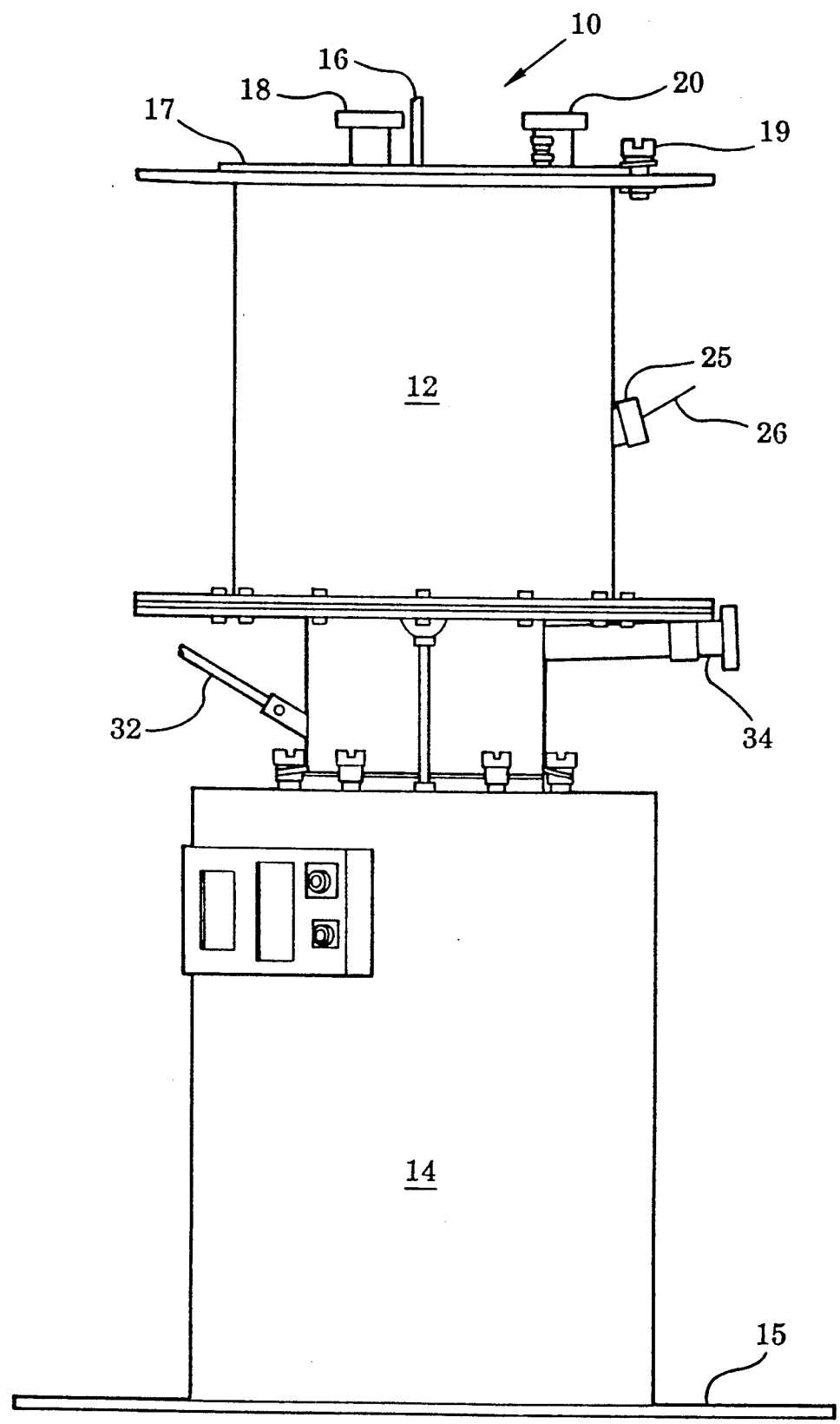
FIG. 1 is a side view showing of the thermal cycling apparatus of the invention.
Figure 2:
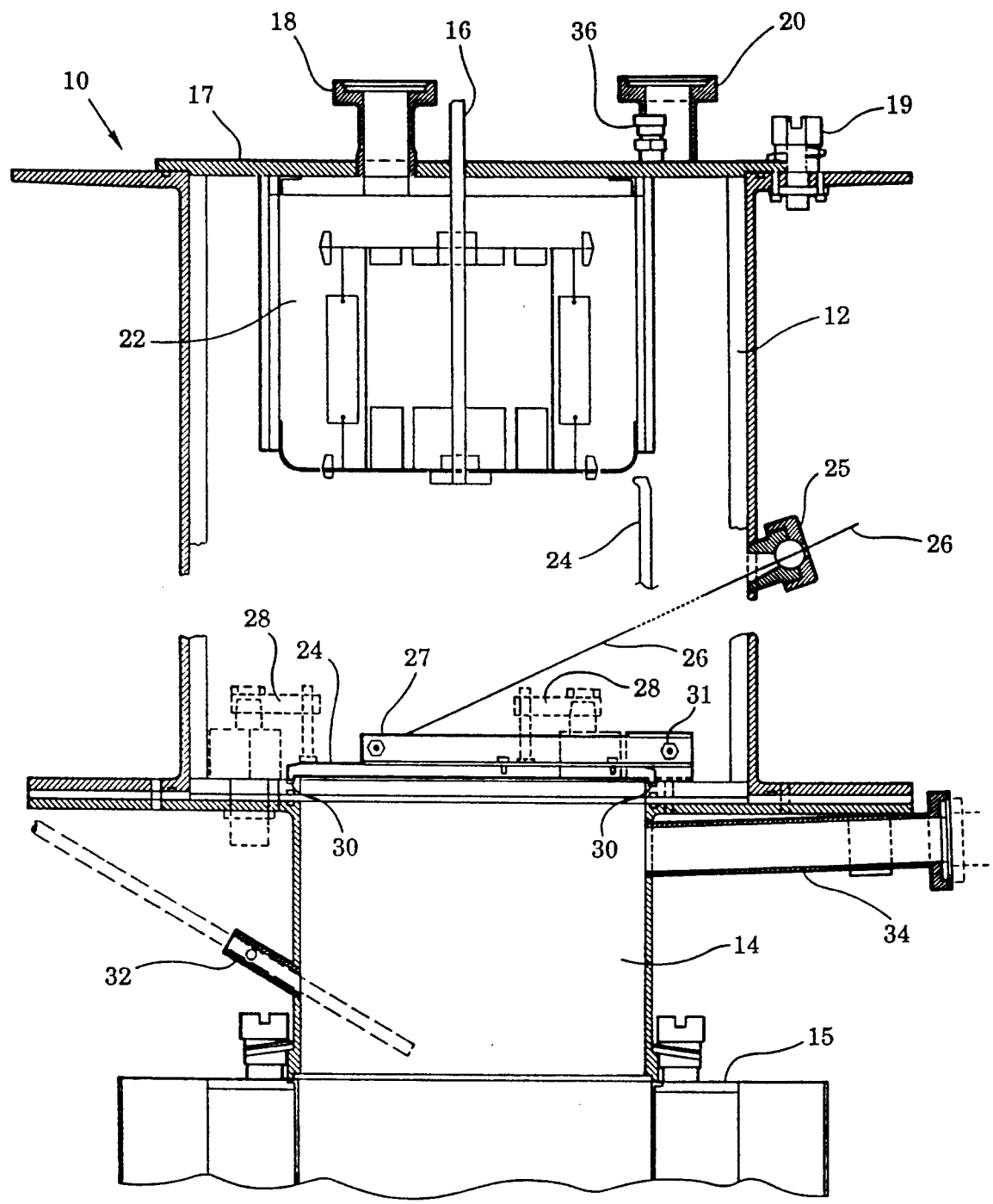
FIG. 2 is a sectional showing of the thermal cycling apparatus of FIG. 1.

Referring now to the drawing Figures and particularly to drawing FIGS. 1 and 2 which depicts a side view and a side view cutaway showing respectfully of the thermal cycling apparatus 10 of the invention. The apparatus comprises an upper heat chamber 12, a lower cool chamber 14 and a support base 15. A rod 16 is used to lower and rise the material specimen between the two chambers 12 and 14 herein after discussed in greater detail. The rod 16 passes through a seal in lid 17 and maintains a sealed relationship therewith at all times. The rod can be constructed from any suitable material suitable for the purpose intended. It has been found that a rod or tube constructed from G10 fiber glass is suitable for this purpose. The lid 17 is held in place by a plurality of quick release clamps 19 around the lid (one shown).

Hot gaseous nitrogen is admitted into the top chamber 12 through a tube 18 in lid 17 and is exited from the chamber through an exit tube 20 also extending through lid 17 to a location externally of the apparatus 10. The gaseous nitrogen is supplied from an external source and can be heated to a maximum temperature of approximately +1000 degrees F. prior to entry into the thermal cycling apparatus 10.

A basket 22 for placement of specimens for cycle testing is attached to the rod 16 and is translatable between the upper and lower chamber via the translation of the rod 16. The rod can be translated manually or by automatic means such as a computer operated motor attached thereto.

A pivotable door 24, depicted in the preferred embodiment as a "flapper" door, separates the upper chamber 12 and the lower chamber 14. A control wire 26 attached to one side of the door, i.e. the pivotal translating side 27, and extends externally of the thermal cycling apparatus 10 through a chamber wall seal 25 and operates the door between its pivoted open position shown in drawing FIGS. 2 and 3 and its pivoted closed position shown in drawing FIG. 4. To operated the door 24 between closed and open positions, the control wire 26 is pulled outwardly from the apparatus 10 and secured in place and for closing the door the control wire is released.

Figure 3:
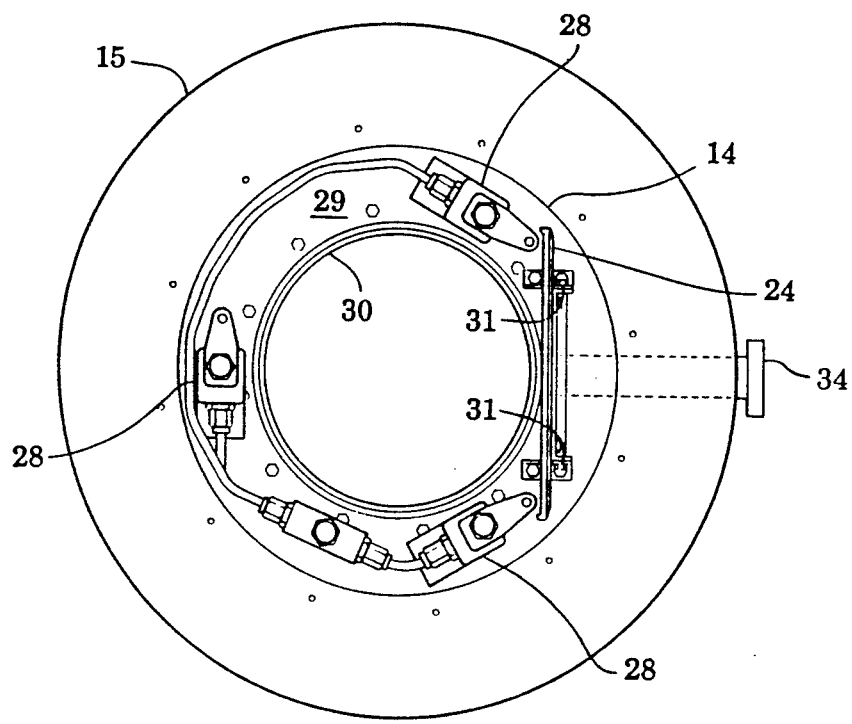
FIG. 3 is a top plan view showing the door between the chambers open.
Figure 4:
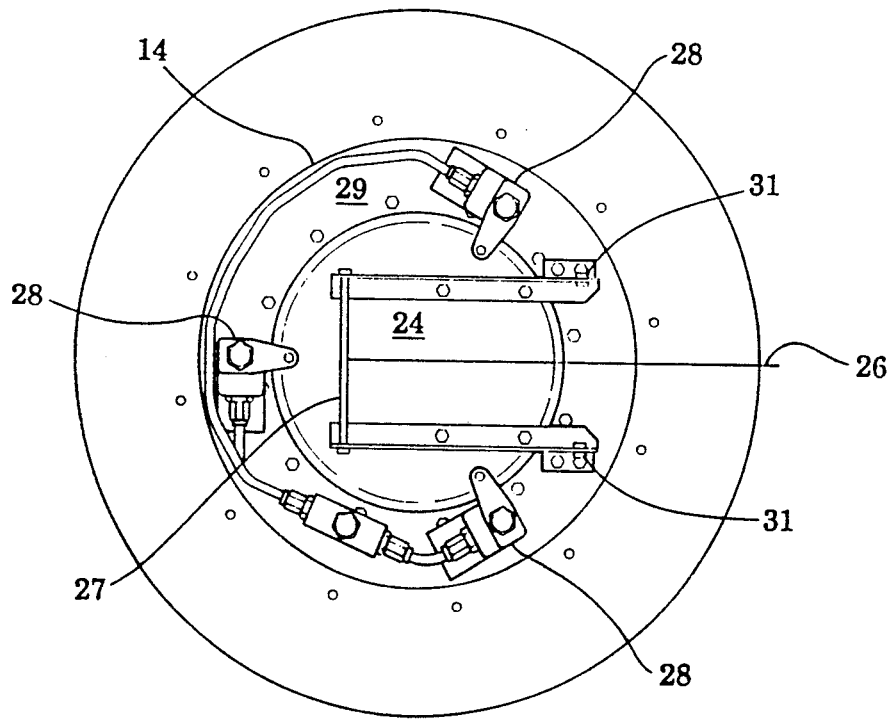
FIG. 4 is a top plan view showing the door between the chambers closed.

As shown in drawing FIG. 4, a plurality of hydraulic clamps 28 are attached to the upper surface seal plate 29 of the lower chamber 14 and are selectively actuated externally of the apparatus to release the door for pivoting about pivots 31 and to seal the door to seat/seal 30 (see FIGS. 2 and 3). The lid is removeably secured in a sealed relationship to the upper surface of the upper chamber 12 by releasable clamps 28. An example of the clamp is a air/hydraulic clamp, CLR 240, manufactured and distributed by Carrlane under the trademark SWIFT SURE. The preferred seat/seal is constructed of TEFLON. Under some specific conditions the clamps 28 may not be required to perfect a perfect seal of the door and its seat.

A fill tube 32 is used to supply cryogenic liquid, preferably hydrogen, to the lower chamber 14. A tube 34 provides a vent from the lower chamber 14 to a location externally of the device.

A sniffer port 36 is provide through the top of the upper chamber 12 the purpose of which is hereinafter discussed.

Sufficient insulation is provide to maintain the upper chamber and lower chamber at their separate desired temperatures.

In operation the lid 17 is removed and the basket 22 is loaded with a specimen or specimens of material or materials for thermal cycle testing. The lid is then closed and sealed. If the lower chamber is not already filled with liquid hydrogen it is filled through fill tube 32. The door 24 is now closed and sealed by the hydraulic cylinders as required. Heated gaseous nitrogen is now forced into the upper chamber until the desired heat is achieved, i.e. from 0 to +1000 F. After the specimen is heated to the desired temperature, the hydraulic cylinders if used are released and the pull wire is pulled to open door 24. The rod 16 is then translated downwardly lowering the basket and specimen(s) into the liquid hydrogen in the lower chamber where it is cooled to −423 F. After the specimen is cooled to −423 F. the basket is translated from the lower chamber to the upper chamber. The door is then closed and sealed and the upper chamber is elevated to the desired temperature. The process is repeated for the number of hot and cold cycles desired. After the cycling is completed, the lid is removed and the material specimen(s) under test is removed from the basket.

Suitable insulation is positioned on the upper chamber lid 17 and the heater chamber surfaces.

While the present invention has been described with reference to a particular embodiment thereof, it will be understood that numerous modifications can be made by those skilled in the art without actually departing from the scope of the invention. Accordingly, all modifications and equivalents may be resorted to which fall within the scope of the invention as claimed.

What is claimed is:

1. A thermal cycling device comprising:
   a first heating chamber;
   a second cooling chamber vertically disposed beneath said first heating chamber;
   a door pivotal between an open and a closed state separating said chambers;
   a wire extending from said door to a location externally of said thermal cycling device for pivoting said door between said states;

means extending externally of said thermal cycling apparatus for translating at least one test specimen between said chambers when said door is in said open state;

means for heating said first chamber and said at least one test specimen positioned therein to an elevated temperature when said door is in said closed state; and means for lowering the temperature in said second chamber to a cryogenic temperature and reducing the temperature of said at least one test specimen to the temperature of said lower chamber when positioned therein.

2. The thermal cycling device of claim 1 wherein said first and second chambers are coaxial.

3. The thermal cycling device of claim 1 wherein said door pivots into said first chamber when pivoting to said open state.

4. The thermal cycling device of claim 1 wherein said means for translating said at least one specimen between chambers comprise a basket attached to a rod an end of which extends externally of the apparatus.

5. The thermal cycling device of claim 1 wherein the means for heating said first chamber comprises a heated gas.

6. The thermal cycling device of claim 5 wherein said gas is gaseous nitrogen.

7. The thermal cycling device of claim 1 wherein said first chamber is heated to a temperature in the range of 0 to +1000 degrees F.

8. The thermal cycling device of claim 1 wherein said means for lowering the temperature in said second chamber is by filling said second chamber with a super cooled liquid selected from a group consisting of liquid nitrogen, liquid hydrogen or liquid helium.

* * * * *